United States Patent [19]

Ayusawa et al.

[11] Patent Number: 4,479,017

[45] Date of Patent: Oct. 23, 1984

[54] PROCESS FOR PRODUCING ETHER COMPOUNDS BY CATALYTIC HYDROGENOLYSIS

[75] Inventors: Tadashi Ayusawa, Yatabe; Tadamichi Aoki; Yutaka Nomura, both of Ami, all of Japan

[73] Assignee: Mitsubishi Petrochemical Co., Ltd., Tokyo, Japan

[21] Appl. No.: 391,304

[22] Filed: Jun. 23, 1982

[30] Foreign Application Priority Data

Jun. 29, 1981 [JP] Japan .................................. 56-99766
Apr. 12, 1982 [JP] Japan .................................. 57-59756

[51] Int. Cl.$^3$ ........................ C07C 41/00; C07C 41/28
[52] U.S. Cl. .................................. 568/613; 568/671; 568/672
[58] Field of Search ............... 568/613, 671, 678, 679, 568/672

[56] References Cited

U.S. PATENT DOCUMENTS

2,425,042 8/1947 McNamee et al. .................. 568/613

FOREIGN PATENT DOCUMENTS

473097 4/1951 Canada .................................. 568/613
727675 2/1966 Canada .................................. 568/678

OTHER PUBLICATIONS

Arundale et al., Chem. Rev., vol. 51, (1952), 526-528.

*Primary Examiner*—Howard T. Mars
*Attorney, Agent, or Firm*—Sherman & Shalloway

[57] ABSTRACT

In a process for producing an ether compound by the catalytic hydrogenolysis of an acetal compound in the presence of a catalyst, the improvement wherein an acetal compound of the following formula (2)

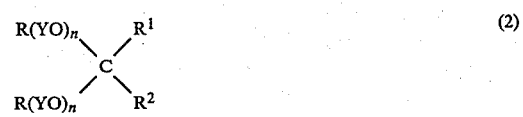

wherein
R represents a hydrogen atom or a lower alkoxy group, Y represents an alkylene group having 2 to 12 carbon atoms, n represents a positive number of from 1 to 6, the two groups $R(YO)_n$ may, together with the carbon atom to which they are bonded, represent a 1,3-dioxolane ring, and $R^1$ and $R^2$, independently from each other, represent a hydrogen atom or a $C_1$–$C_6$ alkyl group, provided that at least one of $R^1$ and $R^2$ represents a hydrogen atom, is catalytically hydrogenolyzed in the presence of a palladium catalyst on a carbon carrier in the absence of an acid substance added, thereby to form an ether compound of the following formula (1)

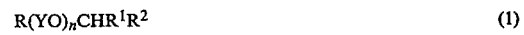

wherein
R, $R^1$, $R^2$, Y and n are as defined.

6 Claims, No Drawings

PROCESS FOR PRODUCING ETHER COMPOUNDS BY CATALYTIC HYDROGENOLYSIS

This invention relates to an improved process for producing an ether compound by catalytically hydrogenolyzing a corresponding acetal compound in the presence of a catalyst. More specifically, it relates to a process for producing an ether compound with a high selectivity and in a high yield by catalytically hydrogenolyzing a formaldehyde acetal or an aldehyde acetal in the presence of a reduced amount of a catalyst at relatively low temperature and pressures without the need to add an acid substance to the reaction system as in a conventional process.

More specifically, this invention relates to a process for producing an ether compound by catalytically hydrogenolyzing an acetal compound in the presence of a catalyst, characterized in that an acetal compound of the following formula (2)

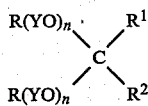  (2)

wherein
R represents a hydrogen atom or a lower alkoxy group, Y represents an alkylene group having 2 to 12 carbon atoms, n is a positive number of 1 to 6, the two groups $R(YO)_n$ may, together with the carbon atom to which they are bonded, represent a 1,3-dioxolane ring, and $R^1$ and $R^2$, independently from each other, represent a hydrogen atom or an alkyl group having 1 to 6 carbon atoms, provided that at least one of $R^1$ and $R^2$ represents a hydrogen atom, is catalytically hydrogenolyzed in the presence of a palladium catalyst on a carbon carrier in the absence of an acid substance added, thereby to form an ether compound of the following formula (1)

$R(YO)_n CHR^1 R^2$  (1)

wherein
R, $R^1$, $R^2$, Y and n are as defined above.

Industrial processes for the production of ether compounds have previously been known which involve catalytically hydrogenolyzing acetal compounds in the presence of catalysts.

For example, as described in M. Freifelder: Practical Catalytic Hydrogenation (1971), page 517, it is known that although the formation of ethers by hydrogenolysis of acetals generally requires high temperatures and high pressures, certain acetals may be hydrogenolyzed to ethers under relatively mild conditions in the presence of an acid substance added.

W. L. Howard et al. [J. Org. Chem. 26, 1026 (1961)] report that an ether was prepared by catalytically hydrogenolyzing a ketal in the presence of an alumina-supported rhodium catalyst in the copresence of an added acid. According to this paper, a vinyl ether is first formed by the effect of the acid and then the hydrogenation of the vinyl ether takes place to give the desired ether, as schematically shown by the following reaction scheme A.

Reaction scheme A

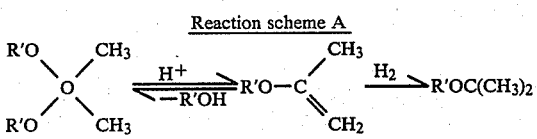

In the above scheme, R' represents a methyl, isopropyl, n-butyl or cyclohexyl group.

This reaction does not proceed under neutral or alkaline conditions.

As a similar reaction, M. Verzele et al. reports that an ether was formed by catalytically hydrogenating a ketone in an acidic alcohol in the presence of a platinum oxide catalyst [J. Chem. Soc., 5598 (1963)].

U.S. Pat. No. 4,088,700 discloses a process for producing an ether compound which comprises catalytically hydrogenolyzing a 1,3-dioxolane, a cyclic acetal of the following formula

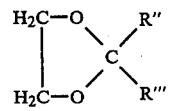

wherein
R" represents a hydrogen atom or an alkyl group having 1 to 4 carbon atoms, and R''' represents an alkyl group having 1 to 20 carbon atoms, a cyclohexyl group, a phenyl group, a tolyl group or a xylyl group, under a relatively high pressure of 900 to 1,200 psi in the presence of a platinum or rhodium catalyst in the copresence of, as an acid substance added, a halide of an element of Group IIIA or a Lewis acid such as $BF_3$ or $AlCl_3$.

Japanese Patent Publication No. 6721/1967 proposes a process for producing an ether, which comprises catalytically hydrogenolyzing a methyl-substituted 1,3-dioxolane, specially 2,2-dimethyl-1,3-dioxolane and 2,2,4-trimethyl-1,3-dioxolane, at relatively low temperatures and pressures in the presence of a rhodium or palladium catalyst, such as a palladium-on-carbon catalyst, in the copresence of phosphoric acid or a $BF_3$ ether complex as an acid substance added.

These processes for producing ether compounds by hydrogenolysis in the presence of acid substances have the disadvantage that the selectivity for the ether compounds is still unsatisfactory and the addition of acid substances is essential.

A process is also known to produce ethers by the catalytic hydrogenolysis of formal (formaldehyde acetal). This process uses high pressures of 50 to 200 atmospheres, and an ether is formed in accordance with the following scheme.

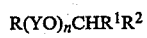

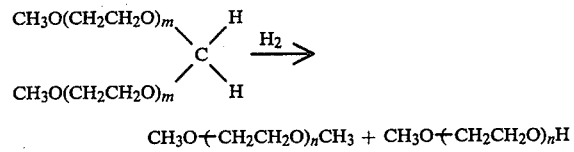

In regard to this type of reaction, Japanese Laid-Open Patent Publication No. 34106/1976 discloses a catalyst comprising nickel, cobalt or copper. Such a catalyst, however, is not entirely satisfactory in regard to activity and selectivity and especially life. In an attempt to solve this problem of the catalyst's life Japanese Laid-Open Patent Publication No. 130612/1978 proposes a catalyst system prepared by adding platinum, rhodium or palladium to nickel, cobalt or copper. This catalyst system has not proved to be entirely satisfactory in regard to its activity and the complexity of its preparation.

The present inventors, too, already proposed the use of a nickel-base composition catalyst comprising nickel, molybdenum, and/or rhenium in order to give a solution to the aforesaid problem (Japanese Laid-Open Patent Publication No. 71031/1981). The catalyst used in this proposal has high activity and selectivity and a long active lifetime in the hydrogenolysis of glycol monomethyl ether formal. But the nickel-containing catalysts used in these proposals have the common feature that their effect is exhibited at a high hydrogen pressure of 50 to 200 atmospheres. The high hydrogen pressure is disadvantageous in industrial practice because of the cost of construction which goes to the reaction apparatus itself and accessory devices such as a compressor, and involves danger in operation. This disadvantage reduces the utility of the process in industrial application.

The present inventors made investigations in order to develop an industrially feasible process for the production of ether compounds by catalytic hydrogenolysis, which can overcome the difficulties and disadvantages of the prior techniques for producing ether compounds from acetals.

These investigations have now led to the discovery that by subjecting acetal compounds of formula (2) given hereinabove including formaldehyde acetal which cannot assume the catalytic hydrogenolyzing mechanism shown in the reaction scheme in the presence of an acid substance as disclosed in the above-cited paper of W. L. Howard et al., namely which cannot go through a vinyl ether intermediate, to a catalytic hydrogenolysis reaction under a set of conditions including the absence of an acid substance and the use of a palladium catalyst supported on a carbon carrier, ether compounds can be produced with markedly increased selectivity and yield from the acetal compounds at relatively low pressures and temperatures in the presence of a reduced amount of the catalyst.

The investigations of the present inventors have shown that by catalytically hydrogenolyzing the acetal compound of formula (2) under the aforesaid combined set of conditions, the reaction readily proceeds at a low pressure of, for example, atmospheric pressure to 10 atmospheres, and the ether compounds of formula (1) can be formed with very high selectivity and in high yields from the acetals of formula (2) including formaldehyde acetal (formal) which cannot go through the vinyl ether intermedite as in scheme (A) given hereinabove.

It has also been found that the use of a palladium-on-carbon catalyst in the presence of an acid substance added, or the use of a palladium-on-alumina catalyst in the absence of an acid substance added cannot achieve the excellent improvement of the process of this invention as will be shown hereinafter by a comparative experiment.

Although we are not in any way bound by theory, we presume from the above facts that the reaction under the combined set of conditions in accordance with this invention differs in mechanism from the reaction shown in (A), and palladium supported on a carbon carrier directly hydrogenolyzes the carbon-oxygen bond of the acetal compound of formula (2) in the absence of an acid substance added.

It is an object of this invention therefore to provide an industrially excellent process for producing the ether compounds of formula (1) from the acetal compounds of formula (2).

The above and other objects and advantages of this invention will become more apparent from the following description.

The starting acetal compound in the process of this invention is an acetal compound of the following formula (2)

wherein R represents a hydrogen atom or a lower alkoxy group, Y represents an alkylene group having 2 to 12 carbon atoms, n represents a positive number of from 1 to 6, the two groups $R(YO)_n$ may, together with the carbon atom to which they are bonded, represent a 1,3-dioxolane ring, and $R^1$ and $R^2$, independently from each other, represent a hydrogen atom or an alkyl group having 1 to 6 carbon atoms, provided that at least one of $R^1$ and $R^2$ represent a hydrogen atom.

Examples of the alkoxy group are those of 1 to 4 carbon atoms such as a methoxy, ethoxy or butoxy group. Examples of the alkylene group are ethylene, propylene and butylene groups when R is a lower alkoxy group, and hexylene and octylene groups in addition to the above exemplified groups when R is a hydrogen atoms.

The starting acetal compound of formula (2) can be easily produced in accordance with a known method by reacting an alcohol and a carbonyl compound, which are industrially inexpensive and easily available, in the presence of an acid catalyst as schematically shown below (see, for example, R. B. Wagner et al., "Synthetic Organic Chemistry", 1953, pages 261 et seq.; R. Leutner "Monatsh", 60, 317 (1932); Japanese Laid-Open Patent Publication No. 108207/1975; and Japanese Laid-Open Patent Publication No. 32598/1979).

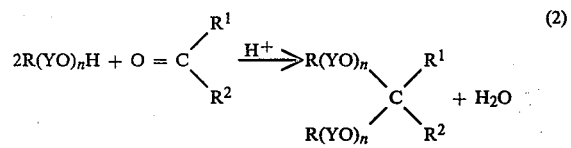

Specific examples of the compound of formula (2) include:

mono(di, tri, or tetra)ethyleneglycol monomethyl ether formal, mono(di, tri or tetra)ethyleneglycol monoethyl ether acetaldehyde acetal, mono(di, tri or tetra)ethyleneglycol monobutyl ether butyraldehyde acetal, mono(di, tri or tetra)ethyleneglycol monoethyl(propyl, or butyl) ether formal, 2-methyl-1,3-dioxolane, di-n-hexyl formal, and di-n-octyl formal.

Preferred compounds of formula (2) are acetal compounds of the following formula (2)'

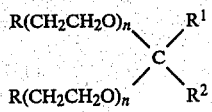

wherein R represents a hydrogen atom or a lower alkoxy group, $R^1$ and $R^2$, independently from each other represent a hydrogen atom or an alkyl group having 1 to 4 carbon atoms, and n is a positive number of from 1 to 4.

Specific examples of the compound of formula (1) produced by the process of this invention include:
mono(di, tri or tetra)ethyleneglycol dimethyl ether,
mono(di, tri or tetra)ethyleneglycol diethyl ether,
mono(di, tri or tetra)ethyleneglycol dibutyl ether,
mono(di, tri or tetra)ethyleneglycol methylether(propyl, or butyl)ether,
ethyleneglycol monoethyl ether,
methylhexyl ether, and
methyloctyl ether.

Preferred compounds of formula (1) are ether compounds of the following formula (1)'

wherein R, $R^1$, $R^2$ and n are as defined with regard to formula (2)'.

According to the process of this invention, the acetal compound of formula (2) is catalytically hydrogenolyzed in the presence of a palladium catalyst supported on a carbon carrier in the absence of an acidic substance added.

The carbon carrier used in the catalyst may include, for example, active carbon, carbon black, graphite and other carbonaceous materials. Carbon black is especially preferred.

There is no particular restriction on the method of depositing a palladium component on the carbon carrier. The palladium component can be deposited on the carbon carrier, if desired cleaned, by any means known per se. For example, there can be used a method which comprises performing the deposition under reducing conditions using an alkali and formaldehyde, a method which comprises performing the deposition in the liquid phase under reducing conditions using hydrogen, a method which comprises depositing a palladium salt on the carbon carrier and reducing it to palladium metal on the carrier using hydrogen or another reducing agent, and other methods [e.g., R. Mozingo "Organic Syntheses" vol. 1, 26, p. 77 (1946)]. There is no restriction on the palladium material used. For example, there can be used palladium chloride, palladium nitrate, palladium hydroxide, acetylacetonate palladium, ammonium (potassium or sodium) palladium chloride, and palladium sulfate. Palladium chloride is usually employed in view of its stability and relatively low price. Generally, palladium chloride is handled as an aqueous hydrochloric acid solution. But since the addition of an acid in the process of this invention rather reduces the activity and selectivity of the catalyst and an alkali metal ion is liable to remain generally in reduction with an alkali-formaldehyde, the catalyst obtained in this case is preferably washed well with water to remove $Cl^-$ ion, $Na^+$ ion, etc.

A palladium catalyst supported on a commercially available carbon carrier may also be utilized. It is preferable in this case to wash it with boiling water, dry it and then again reduce it in a stream of hydrogen gas. The amount of palladium deposited can be properly selected. For example, it is about 0.1 to about 10% by weight, preferably about 0.5 to about 5% by weight.

In the practice of the process of this invention, the catalytic hydrogenolysis must be carried out in the presence of the aforesaid palladium catalyst on a carbon carrier in the absence of an acid substance added. The reaction operation itself can be carried out in accordance with a known technique of catalytic hydrogenolysis.

The reaction temperature is, for example, about 50° to about 300° C., preferably about 100° to about 250° C. The process of this invention has the advantage that under the aforesaid combined set of conditions, the reaction can be carried out under a relatively low hydrogen pressure. For example, the hydrogen pressure is atmospheric pressure to about 200 atmospheres, preferably atmospheric pressure to about 50 atmospheres, more preferably from atmospheric pressure to about 35 atmospheres, especially preferably from atmospheric pressure to about 20 atmospheres.

The reaction can be carried out by contacting at least one acetal compound of formula (2) with hydrogen in a hydrogenolysis zone in the presence of the aforesaid palladium catalyst on a carbon carrier and in the absence of an acid substance such as phosphoric acid, Lewis acids or other acid substances used in the conventional processes. The ether compound (1) can be easily separated from the reaction mixture by, for example, distillation.

The reaction can be performed batchwise while the catalyst is suspended in the starting acetal compound of formula (2) in the reaction zone. Or it can be performed by a continuous mode wherein the acetal compound (2) is continuously fed into the reaction zone, and on the other hand, the resulting ether-containing reaction product is continuously withdrawn in the liquid phase or as a vapor from the reaction zone. It is also possible to mold the catalyst into a suitable shape for a fixed bed method, and perform the reaction by the fixed bed method.

Thus, according to one embodiment of the process of this invention, there can be employed an industrially advantageous continuous method which comprises continuously feeding the compound (2') and hydrogen into the reaction zone, continuously hydrogenolyzing the compound (2') in the zone in the liquid phase, and continuously withdrawing the reaction product as a vapor together with hydrogen gas from the reaction zone. According to this continuous method, it is possible to feed continuously a hydrogen gas and the compound of formula (2') in the liquid phase into a slurry bed having the catalyst suspended in the compound of formula (2'), continuously hydrogenolyze the compound (2') in the liquid phase, and in the meantime, to withdraw continuously the reaction product mixture as a vapor together with the hydrogen gas from the liquid reaction zone. The reaction mixture recovered as a vapor together with the hydrogen gas can be, for example, cooled to liquefy the product, and can be easily separated from the hydrogen. An etherified intermediate, and/or the starting compound which may get mixed with the reaction product mixture can be easily separated from the desired ether compound by such means as distillation.

The hydrogen gas, the intermediate, the starting compound, etc. can be recycled to the reaction zone for re-use as desired. For example, a monoalkyl ether may be recycled to the step of producing the starting acetal, and the acetal compound can be recycled to the step of catalytic hydrogenolysis. The hydrogen gas can be reused in the catalytic hydrogenolysis step.

In performing the reaction, the starting acetal compound (2) may be used without dilution, but if desired, may be diluted with a suitable solvent. Examples of the solvent used for this purpose include inert organic solvents, for example alcohols such as methanol and ethanol, ethers such as dioxane and the ether compounds of formula (1), and hydrocarbons such as cyclohexane and benzene.

The following examples illustrate the process of this invention in greater detail.

CATALYST PREPARATION OF EXAMPLE 1
PdCl$_2$ AQUEOUS SOLUTION

In a 1-liter measuring flask, 12.00 g (7.20 g as Pd) of PdCl$_2$ was added to 25 g of concentrated hydrochloric acid, and deionized water was added to form 1000 ml of a solution. The solution contained 72.0 mg of Pd per 10 ml.

Catalyst preparation

Carbon black (Ketjen Black EC, a tradename for a product of Lion-Akzo Co., Ltd.; specific surface area 858 m$^2$/g) was suspended in 240 ml of 0.4N sodium hydroxide, and the suspension was stirred at 60° C. for 1 hour. It was filtered, washed with 1 liter of boiling water and dried. 4.8 g of the treated carrier was suspended in 100 ml of 0.1N sodium hydroxide and 200 ml of deionized water, and 30 ml of the PdCl$_2$ aqueous solution prepared as above was aded over the course of 45 minutes with stirring. The mixture was further stirred for 1 hour, filtered and washed with 1 liter of boiling water. The product was again suspended in 400 ml of deionized water, and with stirring at 70° C., hydrogen was blown into the suspension for 30 minutes. The product was collected by filtration, washed with 500 ml of boiling water, and dried overnight at 110° C. to prepare a catalyst having about 5% by weight of Pd deposited thereon (which may sometimes be referred to hereinbelow as 5% Pd/K-EC).

CATALYST PREPARATION EXAMPLE 2

Carbon black (#30, a tradename for a product of Mitsubishi Chemical Co., Ltd.; specific surface area 67.8 m$^2$/g) (2.4 g) was suspended in 200 ml of deionized water, and 10 ml of the PdCl$_2$ aqueous solution prepared as in Catalyst Preparation Example 1 was added. With stirring, 0.1 ml of 37% formalin was added over the course of 5 minutes, and then 40 ml of a 0.1N aqueous solution of sodium hydroxide was added. The mixture was heated to 50° C. and maintained at this temperature for 30 minutes. After filtration, the product was washed with 500 ml of boiling water, and dried overnight at 110° C. The dried product was placed in a glass reaction tube, and under a stream of hydrogen gas, it was further reduced at 150° C. for 2.5 hours to prepare a catalyst having about 3% by weight of Pd deposited thereon (which may sometimes be referred to hereinbelow as 3% Pd/#30).

CATALYST PREPARATION EXAMPLE 3

A catalyst having 5% by weight of Pd deposited thereon (to be sometimes referred to hereinbelow as 5%Pd/MA600) was prepared in the same way as in Catalyst Preparation Example 1 except that carbon black (MA 600, a tradename for a product of Mitsubishi Chemical Co., Ltd.; specific surface area 128 m$^2$/g) was used.

CATALYST PREPARATION EXAMPLE 4

A catalyst having 5% by weight of Pd deposited thereon (to be sometimes referred to hereinbelow as 5%Pd/AB) was prepared in the same way as in Catalyst Preparation Example 1 except that acetylene black (a product of Ibigawa Denko Co., Ltd.; specific surface area 64.9 m$^2$/g) was used.

CATALYST PREPARATION EXAMPLE 5

Two grams of a 5%Pd/activated carbon catalyst (Lot No. 3514, a product of Nippon Engelhaldt Co., Ltd.) was washed with 1 liter of boiling water, dried overnight at 110° C., and again reduced in a stream of hydrogen gas in the same way as in Catalyst Preparation Example 2 (the product may sometimes be referred to hereinbelow as 5%Pd/NE).

In the following Examples, acetal compounds were catalytically hydrogenolyzed in the presence of the palladium catalysts prepared in the above examples.

In the following examples, the conversion of formal was based on the charged formal, and therefore corresponds to the mole% of the formal reacted. The selectivities for the diether and monoether are based on the converted formal and correspond to the mole% of these. Based on stoichiometry, the optimum selectivities are 100%, but in the case of non-selective hydrogenolysis, they may exceed 100 mole%. However, in no case, the sum of the selectivities for the diether and the monoether exceeds 200 mole%.

EXAMPLE 1

A 50 ml. electromagnetically stirred glass autoclave was charged with 12.5 g of ethylene glycol monomethyl ether formal and 0.05 g of the 5%Pd/K-EC catalyst obtained in Catalyst Preparation Example 1. The inside of the flask was purged with hydrogen, and the temperature was raised with stirring under a hydrogen pressure of 3.0 kg/cm$^2$.G. When the temperature reached 150° C., the mixture in the flask was maintained at this temperature for 1.5 hours under a hydrogen pressure of 4.0 kg/cm$^2$.G. After the reaction, the stirring was stopped, and the reaction mixture was cooled. The catalyst was separated from it, and the reaction product was analyzed by gas chromatography. The results obtained were as follows:

Formal conversion: 83.2 mole%
Selectivity for ethylene glycol dimethyl ether: 98.2 mole%
Selectivity for ethylene glycol monoethyl ether: 101.6 mole%

These results are given in Table 1 below.

It can be seen from the results obtained that by hydrogenolyzing ethylene glycol monomethyl ether formal, the ether compounds of formula (1) could be obtained with much higher selectivities under much lower pressures using a much smaller amount of catalyst than in the prior art described hereinabove.

EXAMPLE 2

The same reaction as in Example 1 was carried out except that diethylene glycol monomethyl ether formal was used instead of the formal used in Example 1. The results are shown in Table 1.

EXAMPLES 3 TO 6

The procedure of Example 2 was repeated except that 3%Pd/#30 (Example 3), 5%Pd/MA600 (Example 4), 5%Pd/AB (Example 5) and 5%Pd/NE (Example 6) were used respectively instead of the catalyst used in Example 2. The results are shown in Table 1.

EXAMPLE 7

A 100 ml. electromagnetically stirred autoclave was charged with 0.1 g of the 3%Pd/#30 catalyst obtained in Catalyst Preparation Example 2 and 25.0 g of diethyleneglycol monomethyl ether formal. The inside of the reactor was purged with hydrogen, and the temperature was raised under a hydrogen pressure of 10 kg/cm$^2$.G. When the temperature reached 160° C., the hydrogen pressure was adjusted to 20 kg/cm$^2$.G, and the reaction was carried out at 160° C. for 1.5 hours. The results are shown in Table 1.

COMPARATIVE EXAMPLE 1

The same procedure as in Example 2 was repeated except that there was used a catalyst (to be sometimes referred to hereinbelow as 5%Pd/Al$_2$O$_3$) obtained by washing 2 g of 5%Pd/Al$_2$O$_3$ catalyst (Lot No. 63, a product of Nippon Engelhaldt Co., Ltd.) with 1 liter of warm water at 60° C., and again reducing the catalyst in a stream of hydrogen gas in the same way as in Catalyst Preparation Example 2. The results are shown in Table 1.

COMPARATIVE EXAMPLE 2

The same procedure as in Example 7 was repeated except that 0.13 g of concentrated phosphoric acid was added to the reaction system of Example 7. The results are shown in Table 1.

It is seen from the results that when the catalyst reaction is carried out by using the starting material of formula (2) in the presence of the catalyst specified in this invention, the addition of an acid substance greatly reduces the activity and selectivity of the catalyst.

Selectivity for n-octylmethyl ether: 97.6 mole%
Selectivity for n-octyl alcohol: 101.3 mole%

EXAMPLE 9

The same 100 ml. autoclave as used in Example 7 was charged with 0.2 g of the 3%Pd/#30 catalyst obtained in Catalyst Preparation Example 2, 15.0 g of methyldioxolane and 10.0 g of ethylene glycol. The inside of the autoclave was purged with hydrogen, and the temperature was raised with stirring under a hydrogen pressure of 20 kg/cm$^2$.G. When the temperature reached 160° C., the hydrogen pressure was raised to 30 kg/cm$^2$.G and the mixture was maintained at this temperature and pressure for 4 hours. The stirring was stopped, and the reaction mixture was cooled. The catalyst was separated, and the product was analyzed by gas chromatography. The results obtained were as follows:

Conversion of methyldioxolane: 85.5 mole%
Selectivity for ethylene glycol monoethyl ether: 76.1 mole%
Ethylene glycol diethyl ether: 15.4 mole%
Formation of 1 to 2 mole% of diethyl ether and ethanol as by-products was noted.

EXAMPLE 10

A glass flask having a capacity of about 100 ml was used which was equipped with a hydrogen gas introducing inlet, an inlet for introduction of the starting acetal, a protective tube for a thermocouple designed to measure and record the temperature of the liquid reaction phase, and an opening for withdrawing hydrogen gas and a vapor of the product. A fractional distillation tube (the temperature of the product vapor was controlled by passing hot ethylene glycol through an external jacket) was attached to the gas-withdrawing opening. The product vapor was passed through this tube, and then condensed by a cooler with cooling water to separate it from the hydrogen gas. The condensed liquid was recovered from a product receiver. The flask was stirred by using a magnet rotor. The flask was heated by a heating bath such as an oil bath, or by attaching a heater directly to the outside surface of the flask.

The reaction flask was charged with 0.05 g of the catalyst obtained in Catalyst Preparation Example 1 and 30 g of ethylene glycol monomethyl ether formal to form a slurry bed of the catalyst in the formal. Under atmospheric pressure, hydrogen was continuously

TABLE 1

| Example | Catalyst | Conversion of the formal (mole %) | Selectivity (mole %) | |
|---|---|---|---|---|
| | | | Dimethyl ether | Monomethyl ether |
| 1 | 5% Pd/K-EC | 83.2 | 98.2 | 101.6 |
| 2 | 5% Pd/K-EC | 78.3 | 98.5 | 100.9 |
| 3 | 3% Pd/No. 30 | 62.5 | 98.4 | 101.2 |
| 4 | 5% Pd/MA600 | 64.0 | 97.1 | 102.5 |
| 5 | 5% Pd/AB | 49.8 | 95.0 | 103.8 |
| 6 | 5% Pd/NE | 66.3 | 96.4 | 102.7 |
| 7 | 3% Pd/No. 30 | 99.7 | 98.7 | 100.2 |
| Comp. Ex. 2 | 3% Pd/No. 30 + H$_3$PO$_4$ | 55.6 | 71.8 | 74.4 |
| Comp. Ex. 1 | 5% Pd/Al$_2$O$_3$ | 14.3 | 68.9 | 94.6 |

EXAMPLE 8

The procedure of Example 1 was repeated except that di-n-octylformal [(n—C$_8$H$_{17}$O)$_2$CH$_2$] was used instead of the ethylene-glycol monomethyl ether formal. The results obtained were as follows:

Conversion of di-n-octyl formal: 80.4 mole% blown into the slurry bed at a rate of 400 ml/min. The temperature of the top of the fractional distillation tube was adjusted to 70° C. while the temperature of the flask was 170° C. The reaction was carried out at this temperature. The reaction product was continuously withdrawn as a vapor together with the hydrogen gas. The amount of the starting formal to be fed was determined by the amount of the liquid recovered in the product receiver, and the formal was continuously supplied so as to maintain the amount of the liquid in the reactor constant. The reaction was continuously carried out for 30 hours under the aforesaid conditions. The results are shown in Table 2. The analysis of the product was analyzed by gas chromatography. The distillate consisted mainly of a diether, a monoether and the starting formal, and the sum of the amounts of these three compounds was more than 99.8% of the entire products.

TABLE 2

| Time elapsed (hours) | Amount of the distillate (g/hr) | Composition of the distillate (wt. %) | | | Rate of conversion of formal (g/g-cat.-hr) | Rate of formation of the diether | Mole ratio of the diether to the monoether |
|---|---|---|---|---|---|---|---|
| | | Diether | Monoether | Formal | | | |
| 5 | 11.5 | 47.2 | 41.2 | 11.6 | 201 | 108.6 | 0.967 |
| 15 | 11.4 | 47.4 | 41.1 | 11.5 | 200 | 108.1 | 0.974 |
| 30 | 11.5 | 47.3 | 41.0 | 11.7 | 201 | 108.8 | 0.974 |

$$*\text{Rate of conversion of formal} = \left(\begin{array}{c}\text{the molecular}\\ \text{weight of}\\ \text{formal}\end{array}\right) \times \left(\begin{array}{c}\text{amount of}\\ \text{the distillate}\end{array}\right) \times \left(\frac{\text{Proportion of the diether}}{\text{Molecular weight of the diether}} + \frac{\text{Proportion of the monoether}}{\text{Molecular weight of the monoether}}\right) \times \frac{1}{2} \times \frac{1}{\text{Amount of the catalyst (g)}}$$

$$*\text{Rate of formation of the diether} = \frac{\left(\begin{array}{c}\text{amount of the distillate}\end{array}\right) \times \left(\begin{array}{c}\text{proportion of the diether in the distillate}\end{array}\right)}{\text{Amount of the catalyst (g)}}$$

$$*\text{Mole ratio of the diether/monoether} = \frac{\left(\begin{array}{c}\text{Proportion of the diether in the distillate}\end{array}\right) \times (\text{molecular weight of the monether})}{\left(\begin{array}{c}\text{Proportion of the monoether in the distillate}\end{array}\right) \times (\text{molecular weight of the diether})}$$

It is seen from Table 2 that no reduction in activity and selectivity was seen with time, and after the reaction for only 30 hours, the yield of the product was more than 3,000 per unit amount of the catalyst which corresponded to more than 60,000 g/g of Pd.

The ratio of the diether to the monoether shows the selectivity of the reaction. Since the product consisted almost selectively of the diether and monoether, if 0.98 mole of the diether and 1.02 mole of the monoether were obtained from 1 mole of formal, the selectivity for the diether and the selectivity for the monoether were 98% and 102%, respectively. The diether/monoether ratio at this time is 0.96. The results of Table 2 show that the diether formed in a selectivity of more than 98%.

EXAMPLE 11

The procedure of Example 10 was repeated except that diethylene glycol monomethyl ether formal was used as the formal, and the reaction temperature, the temperature of the top of the fractional distillation tube, and the flow rate of hydrogen were changed, respectively, to 185° C., 115° C., and 350 ml/min.

The results of the reaction remained almost unchanged for 15 hours. The results obtained were as follows:
Amount of the distillate: 9.5 g/hr
Composition of the distillate:
  Diether 46.3% by weight
  Monoether 42.1% by weight
  Formal 11.6% by weight
Rate of conversion of formula: 167 g/g-cat.-hr
Diether/monoether ratio: 0.985

COMPARATIVE EXAMPLE 3

The procedure of Example 9 was repeated except that 0.3 g of concentrated phosphoric acid was added. The reaction, however, was stopped in 3 hours because absorption of hydrogen was no longer observed.
The results are shown below.
Conversion of methyldioxolane: 99.5 mole %
Selectivity for ethylene glycol monoethyl ether: 44.3 mole%
Selectivity for ethylene glycol diethyl ether: 40.0 mole%
Formation of 4% of diethyl ether and 2% of ethanol as by-products was noted.

As shown in Comparative Example 2, the addition of an acid substance greatly reduces both the activity and selectivity of the catalyst when the acetal compound is a formal. In the case of the monoalkyldioxolane (acetal compound) of formula (2) used as a starting material in this invention, too, the addition of an acid substance markedly reduces the selectivity for ethylene glycol monoethyl ether.

COMPARATIVE EXAMPLE 4

4.8 g of Sl-1 (powdery $SiO_2$ manufactured by Ketjen Company) was put in 200 ml of deionized water, and with a stirring, 30 ml of the $PdCl_2$ solution prepared in Catalyst Preparation Example 1 was added. The mixture was stirred for 10 minutes, and 90 ml of a 0.11N aqueous solution of ammonia was added over the course of 1 hour. The mixture was further stirred for 1 hour and 20 minutes. Then, with stirring, hydrogen gas was blown at a rate of 1 liter/min. into the solution for 45 minutes. The inside of the flask was purged with nitrogen, and the reaction mixture was filtered. The filtrate was washed with ten 100 ml. lots of warm water at 60° C., dried, and finally reduced at 150° C. for 1.5 hours in a stream of hydrogen gas.

Using the resulting catalyst, the same reaction as in Example 1 was carried out for 1 hour. No absorption of hydrogen occurred, and the conversion of the formal was nearly zero.

COMPARATIVE EXAMPLE 5

A Pd/Celite catalyst was prepared in the same way as in Comparative Example 4 except that Celite was used as a carrier.

The same reaction as in Example 1 was carried out using the resulting catalyst. Analysis of the product showed that the conversion of the formal was as low as 5.0%.

It is seen from Comparative Examples 1, 4 and 5 that when palladium catalysts supported on oxide carriers were used, the conversion of the formal was low.

COMPARATIVE EXAMPLE 6

The same reaction as in Example 2 was carried out except that 0.75 g of aluminum chloride ($AlCl_3$) was used additionally as the catalyst. The results are shown in Table 3.

COMPARATIVE EXAMPLE 7

The same reaction as in Example 2 was carried out except that 1.29 g of a boron trifluoride/ethyl ether complex compound [$(C_2H_5)_2O \cdot BF_3$, 47% by weight of $BF_3$] was additionally used as the catalyst. The results are shown in Table 3. Table 3 also contains the results of Example 2.

TABLE 3

| Run | Catalyst | Conversion of the formal (mole %) | Selectivity (mole %) Dimethyl ether | Selectivity (mole %) Monomethyl ether |
|---|---|---|---|---|
| Comp. Ex. 6 | 5% Pd/K-EC, $AlCl_3$ | 69.1 | 73.4 | 125.3 |
| Comp. Ex. 7 | 5% Pd/K-EC, $(C_2H_5)_2O \cdot BF_3$ | 99.0 | 51.9 | 72.6 |
| Ex. 2 | 5% Pd/K-EC | 78.3 | 98.5 | 100.9 |

The results in Table 3 shows that the addition of the acid catalysts reduces activity or selectivity.

What we claim is:

1. In a process for producing an ether compound by the catalytic hydrogenolysis of an acetal compound in the presence of a catalyst, the improvement wherein an acetal compound of the following formula (2)'

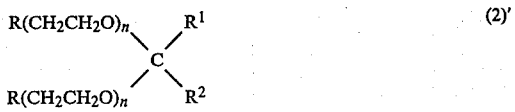

wherein
R represents a hydrogen atom or a lower alkoxy group, n represents a positive number of from 1 to 4, and $R^1$ and $R^2$, independently from each other, represent a hydrogen atom or a $C_1$-$C_4$ alkyl group, provided that at least one of $R^1$ and $R^2$ represents a hydrogen atom, is catalytically hydrogenolyzed in the presence of a palladium catalyst on a carbon carrier in the absence of an acid substance added, thereby to form an ether compound of the following formula (1)'

$$R(CH_2CH_2O)_n CHR^1 R^2 \quad (1)'$$

wherein
R, $R^1$, $R^2$, and n are as defined.

2. The process of claim 1 wherein the catalytic hydrogenolysis is carried out at a temperature of about 50° to about 300° C.

3. The process of claim 1 wherein the catalytic hydrogenolysis is carried out at atmospheric pressure to about 50 atmospheres.

4. The process of claim 1 which comprises continuously hydrogenolyzing the acetyl compound of formula (2)' in the liquid phase in the presence of the palladium catalyst on the carbon carrier without the addition of any acid substance, and continuously recovering the reaction product as a vapor together with the hydrogen gas from the reaction zone, thereby to form an ether compound of the formula (1)'.

5. The process of claim 1 wherein the catalytic hydrogenolysis is carried out at a temperature of from about 100° to about 250° C. and at a hydrogen pressure of from about atmospheric pressure to about 35 atmospheres.

6. The process of claim 4 wherein the catalytic hydrogenolysis is carried out at about atmospheric pressure.

* * * * *